United States Patent [19]

West et al.

[11] 4,283,394
[45] Aug. 11, 1981

[54] CYTOTOXIC NUCLEOSIDE-CORTICOSTEROID PHOSPHODIESTERS

[75] Inventors: Charles R. West, East Amherst; Chung I. Hong, Williamsville, both of N.Y.

[73] Assignee: Research Corporation, New York, N.Y.

[21] Appl. No.: 63,753

[22] Filed: Aug. 6, 1979

[51] Int. Cl.³ ............................................. C07J 17/00
[52] U.S. Cl. ....................................... 424/182; 536/5; 536/6; 536/7
[58] Field of Search ....................... 536/5, 28, 29, 6, 7; 424/180, 182

[56] References Cited

U.S. PATENT DOCUMENTS

| | | | |
|---|---|---|---|
| 3,325,474 | 6/1967 | Sarett et al. | 536/5 |
| 3,904,599 | 9/1975 | Stache et al. | 424/180 |
| 4,083,969 | 4/1978 | Inoue et al. | 424/182 |

*Primary Examiner*—Johnnie R. Brown
*Attorney, Agent, or Firm*—Haight, Rosfeld, & Noble

[57] ABSTRACT

Nucleotides of nucleosides or bases having known cytotoxic activity are reacted with steroids, preferably corticosteroids, to form corresponding cytotoxic nucleoside-corticosteroid phosphodiester analogues of the formula:

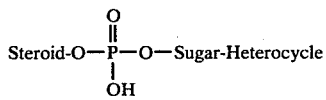

wherein:
  steroid is the residue formed by removal of a hydroxyl hydrogen atom from a natural or synthetic adrenal corticosteroid containing the characteristic cyclopentanophenanthrene nucleus which is esterified to the phosphate moiety at the 21-position;
  sugar is a naturally occurring pentose or deoxypentose in the furanose form, preferably ribose, deoxyribose, lyxose, xylose or arabinose and especially ribose, deoxyribose or arabinose, which is esterified to the phosphate moiety at the 5'-position and covalently bonded to the heterocycle moiety at the 1'-position to form a nucleoside; and
  heterocycle is a purine, pyrimidine, hydrogenated pyrimidine, triazolopurine or similar nucleoside base.

The conjugates exhibit an enhanced therapeutic index as compared to the parent nucleoside or base compounds, and are thus useful cytotoxic, antiviral and antineoplastic agents.

19 Claims, No Drawings

CYTOTOXIC NUCLEOSIDE-CORTICOSTEROID PHOSPHODIESTERS

DESCRIPTION OF THE INVENTION

1. Technical Field of the Invention

This invention relates to a new class of cytotoxic nucleoside-corticosteroid phosphodiesters having useful cytotoxic activity, to methods of using such drugs and to pharmaceutical compositions containing cytotoxically effective amounts of such drugs as a primary active ingredient.

2. Background Art

Cancer can be considered as a group of diseases that can occur in any tissue, organ or system of the body. The causes of all cancers are not known, nor are there any reported major qualitative metabolic differences between cancer cells and host tissue cells of origin. Accordingly, cancer chemotherapy, unlike the chemotherapy of infectious diseases wherein the disease-causing organism itself offers a distinct metabolic or structural biologic target, has far more restrictive fundamental concepts on which to pattern therapeutic treatment.

Most known classes of anticancer drugs exert their action principally because of quantitative differences in metabolic rates of production or levels of certain nucleic acids, enzymes, proteins, hormones, metabolic intermediates, etc., rather than because of qualitative biologic differences between cancer cells and normal cells. Thus, anticancer drugs do not exhibit selective toxicity in the classical sense.

Agents can be taken up selectively into cells and lysosomes via several mechanisms. Once the nucleotide is released from the molecule, the nucleotide is available for conversion into diphosphates, triphosphates, etc. and thereby can exert its cytotoxic effect via a number of possible mechanisms including effects on DNA polymerase, ribonucleoside diphosphate reductase, incorporation into DNA and inhibition of DNA and cellular metabolism in general.

A number of anticancer nucleosides or bases have been described in the prior art. For example, cytosine arabinoside (ara-C), 5-fluorouracil, 5-fluorodeoxyuridine, 6-mercaptopurine and thioguanine have become drugs currently used for the clinical treatment of cancer in human patients. In addition, preliminary clinical trials appear encouraging with respect to a dozen or more other drugs have been reported by H. B. Wood, Jr. in "Drugs with Chemical Activity" and in "Some Unique Compounds in Development" published by the Drug Synthesis and Chemistry Branch, National Cancer Institute, January 1977, the contents of which are incorporated by reference herein. Literally scores of pyrimidines, purines, structurally related heterocyclic bases, nucleosides, etc., have been synthesized and demonstrated to possess high cytotoxic activity in cell culture and in a number of tumor-bearing animals; however, unfavorable therapeutic indexes have restricted the clinical use of this class of antimetabolites to relatively few antineoplastic drugs presently used for the chemotherapy of cancer.

Ara-C is one of the most important antitumor agents currently used in the treatment of acute human myelogenous leukemia and also in combination chemotherapy for the treatment of solid tumors. However, for maximum therapeutic effect, the use of ara-C requires a very complex and precise dosage schedule because of its specific mode of action at the S phase of the cell cycle and of its inactivation by cytidine deaminase. As a result, the plasma half-life of ara-C in patients is generally too short for effective and convenient medication. To overcome this difficulty, a variety of ara-C derivatives including 5'-adamantoyl-ara-C; 5'-palmitoyl-ara-C; $N^4$-adamantoyl-ara-C; and $N^4$-acyl-ara-C have already been synthesized and examined for their therapeutic values as reported by M. Aoshima et al. in Cancer Research 36: 2726 (1976). However, these compounds are too lipophilic to be soluble in aqueous solvent systems.

Glucocortiocids have been used as anti-inflammatory, antitumor and immunosuppresive agents; their applicability in cancer treatment corresponds to the presence of specific steroid hormone receptors which have been identified in the cancerous cell. Prednisolone and prednisone have been used clinically in combination with other drugs in the treatment of human lymphoid leukemias and lymphomas, e.g. see E. S. Henderson et al., Cancer Research 29: 2272 (1969). Furthermore, they exerted synergistic effects in combination therapy, as reported by F. Rosner et al. in Cancer Research 35: 700 (1975), and reduced the toxicity of the agents. However, since the pharmacokinetics, distribution and metabolism of the nucleoside antitumor agents and the steroids are different, the target cells do not necessarily receive both compounds at optimal levels to show any synergistic effect in combination.

Conjugates of the antitumor agents with a natural carrier have shown many advantages including their increased specificity and cell-penetrating properties and reduced toxicity. There have been reports that steroids are used as a carrier of the cytotoxic groups, including nucleoside bases; see J. E. VanLier et al. in Nature 267: 522 (1977).

DISCLOSURE OF THE INVENTION

Accordingly, it is a general object of the present invention to provide cytotoxic drugs which possess unique molecular structures and physicochemical properties in which a steroid portion thereof provides target specificity for cancerous cells having receptors therefor while a nucleoside portion thereof provides anti-tumor activity.

Another object of the present invention is to provide a new class of nucleotide compounds which acts as a new system for the delivery of cytotoxic agents to tumor cells.

An additional object of the present invention is to provide anticancer nucleotides or higher phosphorylated forms of anticancer nucleosides which can be released within the cell via phosphatase enzyme-specific reactions or non-specific mechanisms, thus avoiding or circumventing dependency upon kinase activity or higher phosphorylation mechanisms which are essential for the manifestation of anticancer activity in most prior art clinically used anticancer nucleosides.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing compounds of the general Formula I:

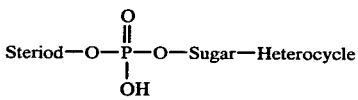

wherein:
- steroid is the residue formed by removal of a hydroxyl hydrogen atom from a natural or synthetic adrenal corticosteroid containing the characteristic cyclopentanophenanthrene nucleus which is esterified to the phosphate moiety at the 21-position;
- sugar is a naturally occurring pentose or deoxypentose in the furanose form, preferably ribose, deoxyribose, lyxose, xylose or arabinose and especially ribose, deoxyribose or arabinose, which is esterified to the phosphate moiety at the 5'-position and covalently bonded to the heterocycle moiety at the 1'-position to form a nucleoside; and
- heterocycle is a purine, pyrimidine, hydrogenated pyrimidine, triazolopurine or similar nucleoside base;

and the physiologically acceptable salts thereof.

It can be seen from Formula I that a number of innovations can be tailored onto the parent molecular structure, including:

(a) Utilization of any combination of monovalent steroid radicals, e.g. corticosteroids, which vary in their degree of unsaturation;

(b) Replacement of ester functions by ether, methylene, amide, etc. functions;

(c) Differences in configuration at the asymmetric carbon, e.g. the R isomer, the S isomer or racemic (RS) mixtures;

(d) Any number of variations in the sugar portions of the molecules, including deoxy forms and variations in stereochemistry of hydroxyl and base substituents; and (e) Variations in the nature of the heterocyclic bases, including any number of pyrimidine, purine or structurally related heterocyclic ring systems.

The physicochemical and metabolic properties of such molecules can be markedly altered by structural modifications in the nature of the hetereocycle, sugar or nucleoside (heterocycle+sugar) stereochemistry as shown in Formula I. It will be appreciated that the cytotoxic nucleotide steroid analogues, as intact molecules, cannot properly be considered as merely derivatives or forms of existing steroids or anticancer nucleotides, but rather are a distinct class of molecules.

Compounds of Formula I can be prepared from starting materials which themselves are known or can be prepared by methods analagous to those known in the art. Suitable steroids are those natural and synthetic adrenal corticosteroids containing the characteristic cyclopentanophenanthrene nucleus and bearing a hydroxyl group at the 21-position; at this is highly reactive to phosphporylation with $POCl_3$ and $(EtO)_3PO$, the presence of additional hydroxyl groups does not pose any practical interference with the reaction. Preferred steroid moieties are 21-hydroxy-1,4-pregnadiene-3,20-diones; 21-hydroxy-1,4-pregnadiene-3,11,20-triones; 21-hydroxy-4-pregnene-3,20-diones; and 21-hydroxy-4-pregnene-3,11,20-triones; the steroid moiety can be substituted by 1-3; e.g. 1 or 2, hydroxy, methyl or fluoro groups at the 2α, 6α, 9α, 11, 16α, 17 or 18 positions of the cyclopentanophenanthrene nucleus.

Suitable such corticosteroids are well known in the art and include but are not limited to betamethasone, chloroprednisone, corticosterone, cortisone, desoxycorticosterone, dexamethasone, dichlorisone acetate, fluocinolone acetonide, fluorohydrocortisone, fluorometholone, fluprednisolone, flurandrenolone, hydrocortisone, methylprednisolone, paramethasone, prednisolone, prednisone, triamcinolone, etc. Compounds of this invention, in addition to those shown in the following Examples, include but are not limited to compounds of the structure shown in Formula I in which the steroid moiety is:

(1) 11β,17α,21-trihydroxy-1,4-pregnadiene-3,20-dione (prednisolone);
(2) 17α,21-dihydroxy-1,4-pregnadiene-3,11,20-trione (prednisone);
(3) 9α-fluoro-11β,17α,21-trihydroxy-16α-methyl-1,4-pregnadiene-3,20-dione (dexamethasone);
(4) 11β,17α,21-trihydroxy-6α-methyl-1,4-pregnadiene-3,20-dione (methyl prednisolone);
(5) 11β,17α,21-trihydroxy-4-pregnene-3,20-dione (cortisol);
(6) 17α,21-dihydroxy-4-pregnene-3,11,20-trione (cortisone);
(7) 11β,21-dihydroxy-4-pregnene-3,20-dione (corticosterone);
(8) 4-pregnen-21-ol-3,20-dione (desoxycorticosterone);
(9) 21-hydroxy-4-pregnene-3,20-dione (corteolone);
(10) 9α-fluoro-11β,17α,21-trihydroxy-4-pregnene-3,20-dione (fluorohydrocortisone);
(11) 11β,21-Dihydroxy-3,20-dioxo-pregn-4-en-18-ol (aldosterone);
(12) 21-Hydroxy-pregna-4,6-diene-3,20 dione (6-dehydro-DOC);
(13) 21-Hydroxy-2α-methyl-pregn-4-ene 3,20-dione (2α-methyl-DOC);
(14) 11β,21-Dihydroxy-pregn-1,4-diene-3,20-dione (1-dehydrocorticosterone);
(15) 16α-Methyl-11β,17α,21-trihydroxy-pregna-1,4-diene-3,20-dione (16α-methyl-prednisolone);
(16) 11β,21-Dihydroxy-16α-methyl-pregna-1,4-diene-3,20-dione;
(17) 9α-Fluoro-11β,17α,21-trihydroxy-16α-methyl-pregn-4-ene-3,20-dione (1,2-dihydrodexamethasone);
(18) 9α-Fluoro-11β,17α,21-trihydroxy-16β-methyl-pregna-1,4-diene-3,20-dione (betamethasone);
(19) 9α-Fluoro-11β,17α,21-trihydroxy-16β-methyl-pregna-1,4-diene-3,20-dione;
(20) 9α-Fluoro-11β,21-dihydroxy-16α,17α-[1-methylethylidene bis(oxy)]-pregna-1,4-diene-3,20-dione (triamcinolone acetonide);
(21) 9α-Fluoro-11β,21-dihydroxy-16α-methyl-pregna-1,4-diene-3,20-dione (desoxymethasone);
(22) 9α-Fluoro-11β,21-dihydroxy-16α-methyl-pregn-4-ene-3,20-dione (1,2,-dihydro-desoxymethasone);
(23) 6α,9α-Difluoro-11β,21-dihydroxy-16α-methyl-pregn-4-ene-3,20-dione; and
(24) 9α,11β-Dichloro-21-hydroxy-16α-methyl-pregna-1,4-diene-3,20-dione.

Nucleotides in general are prepared from corresponding nucleosides by direct phosphorylation using $POCl_3$ and trialkyl-phosphate(s); this method has been used to prepare the 5'-phosphates of cytosine arabinoside and 5-fluoro-2'-deoxyuridine in good yields (60–70 percent, after purification) from the corresponding nucleosides. Conversion of nucleotides to morpholidates has been achieved in excellent yields (about 95 percent). Syntheses utilizing protecting groups or other phosphorylating reagents can be employed for the preparation of nucleotide components, e.g., pyrophosphoryl chloride/m-cresol or o-chlorophenol; di(2-t-butylphenyl9-phosphorochloridate; cyanoethyl phosphate; 2,2-trichlorethyl-phosphorodichloridate; 2,2,2-trichloro-ethyl-2-chlorophenyl-phosphorochloridate; and dinitrobenzyl phosphorochloridate. The direct phosphorylation method is of sufficiently general utility to be an effective procedure to yield adequate quantities of 5'-nucleotides, even if separation of other minor (2' and/or 3') isomers may be required in some instances; this avoids longer synthetic approaches involving protective group chemistry. Chromatographic separation and purification of 5'-monophosphates and final product liponucleotides are then undertaken.

Compounds of this invention, in addition to those shown in the following Examples, include but are not limited to compounds of the structure shown in Formula I in which the nucleoside moiety is:
(1) 1-$\beta$-D-Arabinofuranosylcytosine (ara-C);
(2) 5-Fluorodeoxyuridine (5-FUdR);
(3) 5-Azacytidine;
(4) 1-$\beta$-D-Arabinofuranosyladenine (ara-A);
(5) 6-Mercaptopurine ribonucleoside; or
(6) Tubercidin.

Compounds of this invention which contain a center of asymmetry are ordinarily obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the carboxyl group, or an optically active acid with the amino group, of a suitable compound of this invention. For example, diastereomeric salts of compounds containing a free carboxyl group can be formed with optically active amines, e.g., quinine, cinchonidine, brucine, hydroxyhydrindiamine, morphine, 1-phenylethylamine, 1-naphthylethylamine, phenyloxynaphthyl-methylamine, quinidine and strychnine or basic amino acids, e.g., lysine, arginine and amino acid esters; or diastereomeric salts of basic compounds can be formed with optically active acids, e.g., (+)- and (−)-tartaric acid, dibenzoyl-(+)- and -(−)- tartaric acid, diacetyl-(+)- and -(−)- tartaric acid, camphoric acid, beta-camphorsulfonic acid, (+)- and (−)-mandelic acid, (+)- and (−)- malic acid, (+)- and (−)- 2-phenylbutyric acid, (+)- and (−)-dinitrodiphenic acid or (+)- and (−)- lactic acid. In a similar manner, ester distereomers can be produced by the esterification of compounds containing a free carboxyl group with optically active alcohols, e.g., borneol, menthol or 2-octanol. The resultant mixtures of diastereomeric salts and/or esters can be separated, e.g. by selective crystallization, and the desired optically active compounds can be produced by hydrolytic separation of the isolated diastereomeric compound.

A basic compound of the present invention can be converted into the associated acid addition salt with the use of an acid. For this reaction, suitable acids are those yielding physiologically acceptable salts. Suitable organic and inorganic acids are well known in the art and include but are not limited to aliphatic, alicyclic, araliphatic, aromatic and heterocyclic, mono- or polybasic carboxyic or sulfonic acids e.g. formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicylic acid, phenylpropionic acid, citric acid, gluconic acid, ascorbic acid, nicotinic acid, isonicotinic acid, methanesulfonic acid, ethanedisulfonic acid, $\beta$-hydroxyethanesulfonic acid, p-toluenesulfonic acid, naphthalene mono- and di-sulfonic acids, sulfuric acid, nitric acid, hydrohalic acids, e.g. hydrochloric acid and hydrobromic acid, and phosphoric acids, e.g. orthophosphoric acid.

Due to their cytotoxic and antiviral activity, the compounds of this invention are useful as antibacterial, antiviral and anti-L-1210 leukemic agents. The compounds are effective against the same kinds of cell growth as their corresponding nucleotide parent compounds. In addition to their use in vitro, they can be employed for example, in the oral, injection or perfusion therapy of cancers in substantially the same manner as the corresponding known parent nucleoside or base compounds, e.g. ara-cytidine.

The compounds of this invention can be employed in mixture with convention excipients, i.e. pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g. lubricants, preservatives, stabilizers, wetting agents, emulsifiers, salts for influencing osmotic pressure, buffers, coloring, flavoring or aromatic substances and the like which do not deleteriously react with the active compounds.

For parenteral application, particularly suitable are solutions, preferaly oily or aqueous solutions, as well as suspensions, emulsions or implants, including suppositories. Ampoules are convenient unit dosages.

For enteral application, particularly suitable are tablets, dragees, or capsules having a talc or carbohydrate carrier or binder or the like, the carrier preferably being lactose, corn starch or potato starch. A syrup, elixir or the like can be used wherein a sweetened vehicle is employed. Sustained relese compositions can be formulated including those wherein the active compound is protected with differentially degradable coatings, e.g. by microencapsulation, multiple coatings, etc.

Generally, the compounds of this invention are dispensed in unit dosage form comprising 1–3,000 mg. of a pharmaceutical carrier per each unit dosage and the amount of active agent of the invention per unit dosage is about 1–200 mg.

For topical application, these are employed as viscous to semi-solid or solid non-sprayable forms comprising a carrier indigenous to topical application and having a dynamic viscosity preferably greater than water. Suitable formulations include but are not limited to solutions, suspensions, emulsions, creams, ointments, powders, liniments, salves, aerosols, etc. which are, if desired, sterilized or mixed with auxiliary agents, e.g., preservatives, stabilizers, wetting agents, buffers, salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0.01 to 20 weight percent and are useful in the treatment of psoriasis and Herpes simplex infections.

The compounds of this invention are generally administered to animals, including but not limited to mammals and birds. A cytotoxically effective daily dosage of the active compounds as administered intraperitoneally to mice generally comprises about 10 to 100, preferaly about 50 mg/kg, together with 1–5,000 mg. of pharmaceutically acceptable carrier. The dose can be administered singly or as divided dosages throughout the day.

It will be appreciated that the actual preferred amounts of active compounds used will vary according to the specific compound being utilized, the particular compositions formulated, the mode of application, and the particular situs and organism being treated. Many factors that modify the action of the drug will be taken into account by those skilled in the art, e.g. age, body weight, sex, diet, time of administration, route of administration, rate of excretion, drug combinations, reaction sensitivities and severity of the condition being treated. Optimal application rates for a given set of conditions can be ascertained by those skilled in the art using conventional dosage determination tests in view of the above guidelines and will generally not exceed molar dosage rates conventionally used for the parent nucleotide moiety in the conjugates.

While not a presently preferred utility, the compounds of the present invention are also useful as intermediates in the production of other drugs, e.g. the parent nucleoside or nucleotide and/or steroid compounds can be regenerated by conventional hydrolysis of the phosphate ester bonds.

Monovalent heterocyclic ring substituents encompassed by the present invention are generally of 5–10, preferably 6–10 ring atoms of which 1–4, generally 1–3 and preferably 1 or 2, are oxygen, nitrogen and/or sulfur heteroatoms. The heterocyclic ring can be nonhydrogenated, e.g., imidazolyl, thiazolyl, etc.; partially hydrogenated, e.g., imidazolinyl, oxazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms, e.g., pyrazolyl, imidazolyl, oxazolyl, oxazolinyl, isoxazolyl, isoxazolinyl, thiazolyl or thiazolinyl; a five member heterocyclic ring containing three heteroatoms, e.g., triazolyl, oxadiazolyl, thiadiazolyl, dioxazolyl and oxathiazolyl; or a five member heterocyclic ring containing four heteroatoms, e.g., tetrazolyl, oxatriazolyl and thiatriazolyl.

Suitable heterocyclic groups can be those derived from a six member heterocyclic ring containing a single heteroatom, e.g., pyridyl and pyranyl, preferably tetrahydropyridyl; a six member heterocyclic ring containing two ring heteroatoms, e.g., thiopyranyl, dioxinyl, pyridazinyl, pyrazinyl, piperazinyl, oxazinyl and morpholino, preferably pyrimidinyl, dihydropyrimidinyl and tetrahydropyrimidinyl; or a six member heterocyclic ring containing three ring heteroatoms, e.g., triazinyl, oxathiazinyl and oxadiazinyl, preferably triazinyl. Preferred heterocyclic groups derived from a six member heterocyclic ring are tetrahydropyridyl, pyrimidinyl, dihydropyrimidyl, tetrahydropyrimidyl and triazinyl.

Suitable heterocyclic groups can furthermore be those derived from a fused heterocyclic ring containing one or two six-membered rings fused to a five-membered ring wherein the six-membered ring is preferably interrupted by two nitrogen atoms and wherein the five-membered ring contains one or two, preferably two nitrogen or sulfur heteroatoms, e.g, purine and triazolopurine.

Preferred heterocyclic bases for the compounds of Formula I include but are not limited to cytosine, uracil, thymine, adenine, guanine, dihydrouracil, 5-fluorouracil, 5-azauracil, 6-azauracil, 5-azacytosine, 6-azacytosine, tetrahydropyridine dione, 2-amino tetrahydropyridine dione, 6-mercaptopurine, thioguanine, selenoguanine, 8-azaadenine-7-carboxamide, N-methyl-2-amino-1,2,4-triazolopurine and analogues thereof.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperature are set forth uncorrected in degrees Celsius; unless otherwise indicated, all parts and percentages are by weight. The values obtained in elemental analyses are within commonly accepted limits of error.

1-$\beta$-D-Arabinofuranosylcytosine (ara-C) conjugates of prednisolone, prednisone, dexamethasone, 6$\alpha$-methylprednisolone, cortisol and cortisone, through a phosphodiester bond, were synthesized in order to improve the therapeutic index of ara-C by: (1) being resistant to cytidine deaminase, (2) increasing their cell-penetrating properties, (3) serving as sustained release froms of parent nucleosides, (4) exerting synergistic effects with glucocorticoids after enzymatic hydrolysis of the conjugates, (5) reducing ara-C toxicity and (6) providing target specific antitumor agents.

Melting points were determined in capillary tubes on Mel-Temp apparatus. UV spectra were recorded with a Beckman Acta V spectrophotometer and IR absorptions were determined with a Perkin-Elmer 297 infrared spectrophotometer with KBr pellets. NMR spectra were obtained with a Varian XL-100 spectrometer using Me$_4$Si as an internal standard. AG1-x8 (formate) (Bio-Rad), diethylaminoethyl cellulose (DE-52 Whatman), and cellulose powder (CC 31, Whatman) were used for column chromatography. Evaporations were performed in vacuo at 30° C.

TLC was carried out on glass plates coated with a 0.25 mm layer of silica gel PF-254 (Brinkman) and on polygram SilG UV 254 plates (Brinkman). Paper chromatography was performed by descending manner on Whatman No. 3 MM paper using the following solvent systems: (A) i-PrOH: H$_2$O: concentrated NH$_4$OH (7:2:1); (B) EtOAc: n-PrOH: H$_2$O (4:1:2); and (C) EtOH: 0.5 M NH$_4$OAc, pH 7.5 (5:2).

EXAMPLE 1

N$^4$,2',3'-Triacetyl-1-$\beta$-D-arabinofuranosylcytosine-5'-phosphate (TriAcAra-CMP Starting Material)

A mixture of 1.62 g (5 mmol) of dried ara-CMP, 30 ml of Ac$_2$O and 60 ml of anhydrous pyridine was stirred at room temperature for 18 h and 20 ml of H$_2$O was then added to the ice-cooled mixture. After stirring the mixture at room temperature for 2 h, it was evaporated to dryness and the syrup was evaporated with pyridine 3 times. TLC monitoring of the syrup in solvents A and C showed one spot and the mobilities were identical with those of the compound prepared by phosphorylation of $N^4$, 2',3'-triacetyl-1-$\beta$-D-arabinofuranosylcytosine with $POCl_3$ and $(EtO)_3PO$; TLC, Rf (A) 0.19, Rf (C) 0.56. The UV max of the pyridine free compound taken in 50 percent EtOH showed 243 and 290 nm. The syrupy compound was employed for synthesis of the conjugates without further purification.

EXAMPLE 2

5'-(Prednisolone-21-phosphoryl)-1-$\beta$-D-arabinofuranosylcytosine (I)

TriAcAraCMP, prepared by acetylation of 1.62 g (5 mmol) of ara-CMP with $Ac_2O$ (30 ml) and pyridine (60 ml) as described above, was stirred with 3.60 g (10 mmol) of prednisolone and 4.12 g (20 mmol) of N,N'-dicyclohexyl-carbodiimide (DCC) in 250 ml of anhydrous pyridine at room temperature for 2 days. Water (10 ml) was then added and the suspension was stirred at room temperature overnight.

After evaporating to dryness, the residue was co-evaporated with toluene (10 ml) and extracted with 100 ml of 50 percent EtOH. The insoluble urea was filtered and washed with 50 percent EtOH (20 ml). The combined filtrate was evaporated to dryness and the residue was stirred in 200 ml of 2.5 N $NH_3$-MeOH at room temperature overnight followed by evaporating to dryness. The residue was dissolved in 50 ml of 50 percent EtOH and the solution was applied to a DE-52 (acetate) column (200 g, 5×25 cm) prepacked in 50 percent EtOH. The column was then eluted by gradient with 0–1.5 N AcOH in 50 percent EtOH (1 L each). The eluate between 1250–2000 ml was evaporated to dryness and the residue was treated with $Me_2CO$. The resulting white solid was filtered and washed with $Me_2CO$ followed by drying in vacuo at 30° C.: yield 1.03 g (31 percent).

The analytical sample (as an $NH_4$ salt) was prepared by passing the product (200 mg) through a cellulose column (30 g, 2.5×23 cm) with solvent A as described by C. I. Hong et al. in J. Med. Chem 18: 465 (1975): mp 210°–220° C. slow dec.; TLC Rf(A) 0.60, Rf(B) 0.02, Rf(C) 0.72; UV max ($H_2O$) 242 nm (Epsilon 20,300), 260 sh (18,100); (0.1 N HCl) 250 nm sh (Epsilon 16,700), 268 (17,900); (0.1 N NaOH) 240 nm (Epsilon 19,400), 260 sh (17,100); IR (KBr) 3400 ($NH_2$), 1740 (C=O), 1657, 1610 (C=C, C=N), 1220 (P=O), 1080 and 1055 cm$^{-1}$ (POC); NMR ($Me_2SO$-$d_6$) $\delta$ 0.80 (s, 3, $CH_3$), 1.40 (s, 3, $CH_3$), 0.94–2.40 (br m, 13H), 3.96–5.40 (br, m, 13H), 5.94 (s, 1, $C_4$-H) 6.07 (d, 1, J=4 Hz, $C_1'$-H), 6.09 (d, 1, J=8 Hz, cytosine $C_5$-H), 6.18 (d, 1, J=10 Hz, $C_2$-H), 7.37 (d, 1, -10 Hz, $C_1$-H), 8.07 (d, 1, J=8 Hz, cytosine $C_6$-H), 9.48 (br s, 2, $NH_2$).

Elemental analysis for $C_{30}H_{39}N_3O_{12}P.NH_4.3H_2O$: Calc.: C, 48.91; H, 6.70; N, 7.61; P, 4.20. Found: C, 48.84; H, 6.63; N, 7.88; P, 3.97.

EXAMPLE 3

5'-(Prednisone-21-phosphoryl)-1-$\beta$-D-arabinofuranosylcytosine (II)

Compound II was prepared by condensation of TriAcAra-CMP (1.62 g, 5 mmol) with 3.58 g (10 mmol) of prednisone in the presence of 4.12 g (20 mmol) of DCC in 250 ml of anhydrous pyridine and subsequent removal of the protective groups in 2.5 N $NH_3$-MeOH (200 ml) as described above. The product was separated by a DE-52 column (acetate) with a linear gradient of AcOH (0 to 1.5 N) in 50 percent EtOH (1 L each) as described above. The eluate between 1300–2000 ml was evaporated to dryness and the residue was treated with $Me_2CO$. The white solid was filtered and washed with $Me_2CO$ followed by drying in vacuo at 30° C.: yield 0.95 g (28.6 percent).

The analytical sample (as an $NH_4$ salt) was prepared as described above: mp 210°–220° C. slow dec.; TLC Rf(A) 0.62, Rf(B) 0.02, Rf(C) 0.70; UV max ($H_2O$) 238 nm (Epsilon 21,800), 260 sh (17,700); (0.1 N HCl) 244 nm (Epsilon 16,600), 268 (16,600); (0.1 N NaOH) 236 nm (Epsilon 21,400), 260 sh (16,700); IR (KBr) 3300 ($NH_2$), 1720, 1705 (C=O), 1655, 1610 (C=C, C=N), 1220 (P=O), 1080 and 1040 cm$^{-1}$ (POC); NMR ($Me_2SO$-$d_6$) $\delta$ 0.52 (s, 3, $CH_3$), 1.38 (s, 3, $CH_3$), 0.62–2.30 (br m, 13H), 3.95–5.36 (br m, 11H), 5.91 (d, 1, J=8 Hz, cytosine $C_5$-H), 6.04 (s, 1, $C_4$-H), 6.06 (d, 1, J=4 Hz, $C_1'$-H), 6.12 (d, 1, J=10 Hz, $C_2$-H), 7.64 (d, 1, J=10 Hz, $C_1$-H), 7.88 (d, 1, J=8 Hz, cytosine $C_6$-H), 8.48 (br s, 2, $NH_2$).

Elemental analysis for $C_{30}H_{37}N_3O_{12}P.NH_4.2H_2O$: Calcd. C, 50.27; H, 6.33; N, 7.82; P, 4.32. Found: C, 50.12; H, 6.70; N, 7.70; P, 4.19.

EXAMPLE 4

5'-(Dexamethasone-21-phosphoryl)-1-$\beta$-D-arabinofuranosylcytosine (III)

Compound III was prepared by condensation of TriAcAra-CMP (1.62 g, 5 mmol) with 2.0 g (5.1 mmol) of dexamethasone in the presence of 4.12 g (20 mmol) of DCC in 250 ml of anhydrous pyridine for 2 days and then by adding the additional dexamethasone (393 mg, 1 mmol) followed by reacting for one more day and subsequent removal of the protective groups in 2.5 N $NH_3$-MeOH (200 ml) as described above. The product was separated by a DE-52 column (acetate) with a linear gradient of AcOH (0 to 1.5 N) in 50 percent EtOH (1 L each) as described above. The eluate between 1080–1280 ml was evaporated to dryness and the residue was treated with $Me_2CO$. The solid was filtered and washed with $Me_2CO$ followed by drying in vacuo at 30° C.: yield 350 mg (10 percent).

The analytical sample (as an $NH_4$ salt) was prepared as described above: mp 215°–220° C. slow dec.; TLC Rf(A) 0.80, Rf(B) 0.04, Rf(C) 0.84; UV max ($H_2O$) 237 nm (Epsilon 23,400), 260 sh (17,700); (0.1 N HCl) 240 nm (Epsilon 17,900), 272 (17,900); (0.1 N NaOH) 246 (Epsilon 20,500), 260 (16,000); IR (KBr) 3400 ($NH_2$), 1720, 1665, 1620 (C=O, C=C, C=N), 1225 (P=O), 1070 and 1040 cm$^{-1}$ (POC).

Elemental analysis for $C_{31}H_{40}FN_3O_{12}P.NH_4.2H_2O$: Calcd. C, 49.61; H, 6.44; N, 7.46; P, 4.13. Found: C, 49.45; H, 6.72; N, 7.33; P, 4.21.

EXAMPLE 5

5'-(6$\alpha$-Methylprednisolone-21-phosphoryl)-1-$\alpha$-D-arabinofuranosylcytosine (IV)

Compound IV was prepared by condensation of TriAcAra-CMP (1.46 g, 4.5 mmol) with 1.72 g (4.6 mmol) of 6$\alpha$-methylprednisolone in the presence of 4.12 g (20 mmol) of DCC in 250 ml of anhydrous pyridine for 3 days and subsequent removal of the protective groups in 2.5 N $NH_3$-MeOH (200 ml) as described above. The product was separated by a DE-52 column (acetate) with a linear gradient of AcOH (0 to 1.5 N) in 50 percent EtOH (1 L each) as described above. The eluate between 1250–1800 ml was evaporated to dryness and the residue was treated with Me$_2$CO. The solid was filtered and washed with Me$_2$CO followed by drying in vacuo at 30° C.: yield 400 mg (13.1 percent).

The analytical sample (as an NH$_4$ salt) was prepared as described above; mp 210°–215° C. slow dec.; TLC Rf(A) 0.79, Rf(B) 0.03, Rf(C) 0.84; UV max (H$_2$O) 240 nm (Epsilon 18,600), 260 sh (16,000); (0.1 N HCl) 252 sh (Epsilon 16,200), 270 (17,400); (0.1 N NaOH) 240 (Epsilon 19,300), 260 sh (17,100); IR (KBr) 3400 (NH$_2$), 1725, 1655, 1610 (C=O, C=C, C=N), 1210 (P=O), 1080 and 1030 cm$^{-1}$ (POC).

Elemental analysis for C$_{31}$H$_{41}$FN$_3$O$_{12}$P.NH$_4$.2.75 H$_2$O: Calcd. C, 49.89; H, 6.82; N, 7.51; P, 4.15. Found: C, 49.49; H, 7.20; N, 7.94; P, 4.06.

EXAMPLE 6

5'-(Cortisol-21-phosphoryl)-1-β-D-arabinofuranosylcytosine (V)

Compound V was prepared by condensation of TriAcAra-CMP (1.62 g, 5 mmol) with 3.63 g (10 mmol) of cortisol in the presence of 4.12 g (20 mmol) of DCC in 250 ml of anhydrous pyridine for 3 days and subsequent removal of the protective groups in 2.5 N NH$_3$-MeOH (200 ml) as described above. The product was separated by a DE-52 column (acetate) with a linear gradient of AcOH (0 to 1.5 N) in 50 percent EtOH (1 L each) as described above. The eluate between 1230–1530 ml was evaporated to dryness and the residue was treated with Me$_2$CO. The solid was filtered and washed with Me$_2$CO followed by drying in vacuo at 30° C.: yield 589 mg (18 percent).

The analytical sample (as an NH$_4$ salt) was prepared as described above: mp 215°–225° C. slow dec.; TLC Rf(A) 0.78, Rf(B) 0.02, Rf(C) 0.82; UV max (H$_2$O) 243.5 nm (Epsilon 22,580) 266 sh (14,410); (0.1 N HCl) 250 (Epsilon 20,180), 275 (16,600); (0.1 N NaOH) 241 (Epsilon 24,260), 260 sh (17,310); IR (KBr) 3380 (NH$_2$), 1720, 1650, 1615 (C=O, C=C, C=N), 1230 (P=O), 1080 and 1055 cm$^{-1}$ (POC).

Elemental analysis for C$_{30}$H$_{41}$N$_3$O$_{12}$P.NH$_4$.2 H$_2$O: Calcd. C, 49.99; H, 6.85; N, 7.77; P, 4.30. Found: C, 50.02; H, 6.87; N, 7.52; P, 4.31.

EXAMPLE 7

5'-(Cortisone-21-phosphoryl)-1-β-D-arabinofuranosylcytosine (VI)

Compound VI was prepared by condensation of TriAcAra-CMP (1.62 g, 5 mmol) with 3.61 g (10 mmol) of cortisone in the presence of 4.12 g (20 mmol) of DCC in 250 ml of anhydrous pyridine for 3 days and subsequent removal of the protective groups in 2.5 N NH$_3$-MeOH (200 ml) as described above. The product was separated by a DE-52 column (acetate) with a linear gradient of AcOH (0 to 1.5 N) in 50 percent EtOH (1 L each) as described above. The eluate between 1230–1910 ml was evaporated to dryness and the residue was treated with Me$_2$CO followed by drying in vacuo at 30° C.; yield 665 mg (20 percent).

The analytical sample (as an NH$_4$ salt) was prepared as described above: mp 220°–230° C. slow dec.; Rf(A) 0.77, Rf(B) 0.02, Rf(C) 0.82; UV max (H$_2$O) 240 nm (Epsilon 19,740) 270 sh (12,100); (0.1 N HCl) 245 (Epsilon 15,530), 274 (14,740); (0.1 N NaOH) 236 (Epsilon 20,260), 260 sh (12,630); IR (KBr) 3380 (NH$_2$), 1725, 1705 (C=O), 1675, 1655 (C=C, C=N), 1220 (P=O), 1070 and 1050 cm$^{-1}$ (POC).

Elemental analysis for C$_{30}$H$_{39}$N$_3$O$_{12}$P.NH$_4$.1.75 H$_2$O: Calcd. C, 50.44; H, 6.56; N, 7.84; P, 4.34. Found: C, 50.67; H, 6.96; N, 7.55; P, 4.11.

EXAMPLE 8

Recovery of Ara-CMP

In each separation procedure of the ara-C conjugate, the subsequent eluate after the product fractions and the washing of the column with 2 N HOAc (500 ml) were pooled and evaporated at 25° C. in vacuo. The residue was treated with Me$_2$CO, the solid was collected on a filter and washed with Me$_2$CO followed by drying in vacuo at 30° C. Usually 50 percent of the ara-CMP was recovered, which could be used for more synthesis of the ara-C conjugates.

EXAMPLE 9

Characterization of Conjugate Structures

Structures of the conjugates, which had already been verified by elemental analyses, UV, IR and NMR spectra, were further characterized by chemical and enzymatic hydrolysis of the phosphodiester bond. Hydrolysis of pred-p-ara-C and prednisone-p-ara-C by 0.1 N Ba(OH)$_2$ resulted in prednisolone-21-phosphate and ara-C and prednisone-21-phosphate and ara-C, respectively. The steroid phosphates were each further hydrolyzed to the corresponding steroid. Alternatively, the enzymatic hydrolysis of the conjugates gave the corresponding steroid and ara-CMP and the latter was further hydrolyzed to ara-C by 5'-nucleotidase.

EXAMPLE 10

Enzyme Sensitivity Studies

Enzymatic cleavage of the phosphodiester bond of the conjugates was studied by incubating the conjugates (5 μmol) with various enzymes (1.5–3 mg) in appropriate buffer and with plasma (final volume 0.5 ml). An aliquot (200 μl) of the 24 h incubation mixtures was streaked on Whatman 3 MM paper (23×57 cm) with the authentic markers and the paper was developed in Solvent A. The bands were characterized and analyzed semi-quantitatively by UV estimation of the chromatographs. The conjugates were found to be resistant to enzymatic hydrolysis by alkaline phosphatases (occurring in practically all animal and human tissues) while being relatively sensitive to phosphodiesterase, 5'-nucleotidase and acid phosphatase. The conjugates also remained 60–85 percent intact during the incubation with baboon plasma at 37° C. for 24 h. From the results of these tests, conjugates of this type appear capable of serving as sustained release froms of the parent steroid and nucleoside components thereof.

A. Phosphodiesterase I

The conjugate (5 μmol) was incubated with 1 M Tris-HCl, pH 8.8 (0.05 ml) and purified phosphodiesterase I from *Crotalus adamenteus* (1.5 mg., Sigma Chemical Co.) in 0.45 ml. of H$_2$O for 24 h at 37° C. Both pred-p-ara-C (I) and prednisone-p-ara-C (II) hydrolyzed completely, the products being ara-CMP (40 percent), ara-C (10 percent) and prednisolone or prednisone (50 percent).

B. Snake Venom

Following the protocol of Example 9(A) but using 2.5 mg. of crude *Crotalus adamenteus* venom, both pred-p-ara-C (I) and prednisone-p-ara-C (II) were hydrolyzed completely, the products being ara-C (50 percent) and the steroid (50 percent).

C. 5'-Nucleotidase

The conjugate (5 μmol) was incubated with 1 M Tris-HCl, pH 9.0 and 0.05 M MgSO$_4$ (0.05 ml) and purified 5'-nucleotidase from Crotalus adamenteus (2 mg., Sigma Chemical Co.) in 0.45 ml. of H$_2$O for 24 h at 37° C. Both pred-p-ara-C (I) and prednisone-p-ara-C (II) hydrolyzed completely, the products being ara-C (50 percent) and prednisolone or prednisone (50 percent).

D. Acid Phosphatase

The conjugate (5 μmol) was incubated with 0.15 M NaOAc, pH 4.8 (0.05 ml) and crude wheat germ acid phosphatase (3 mg., Sigma Chemical Co.) in 0.45 ml. of H$_2$O at 25° C. for 24 h. Pred-p-ara-C (I) was 86 percent hydrolyzed, the products being pred-p-ara-C (8 percent), ara-CMP (5 percent), ara-C (42 percent) and prednisolone (45 percent). Prednisone-p-ara-C (II) was 88 percent hydrolyzed, the products being prednisone-p-ara-C (7 percent), ara-CMP (4 percent), ara-C (43 percent) and prednisone (46 percent).

E. Alkaline Phosphatase

Neither of the conjugates was hydrolyzed when 5 μmol thereof was incubated with 1 M Tris-HCl, pH 8.0 (0.05 ml) and bacterial alkaline phosphatase (0.1 ml suspension, Worthington Biochemical Corp) in 0.35 ml. of H$_2$O at 25° C. for 24 h.

F. Plasma

The conjugate (5 μmol) was incubated with 0.5 ml of fresh baboon plasma at 37° C. for 24 h. 39 percent of the pred-p-ara-C (I) was hydrolyzed, the products being pred-p-ara-C (44 percent), ara-UMP (7 percent), ara-U (21 percent) and prednisolone (28 percent). Only 15 percent of the prednisone-p-ara-C (II) was hydrolyzed, the products being prednisone-p-ara-C (74 percent), ara-UMP (13 percent) and prednisone (13 percent).

EXAMPLE 11

Antiproliferative Activity in vitro

The antiproliferative activity of the conjugates, ara-C, ara-CMP and the steroids was determined by measuring their effects against mouse leukemia L-1210 cells in culture. The assay was performed in test tubes without agitation according to the procedure described by Hong et al. in J. Med. Chem. 16: 139 (1973). After 24, 48 and 72 h, viable cell counts were performed on the cultures which had been incubated with compounds in various concentrations and the concentration of each compound required to produce a 50 percent inhibition of growth (ED$_{50}$) after 72 h was determined by interpolation using the method described by Tritsch et al. in Cancer Biochem. Biophys. 2: 87 (1977). The results are shown in Table I.

Pred-p-ara-C (I), DXM-p-ara-C (III), MePred-p-ara-C (IV) and cortisone-p-ara-C (VI) exhibited activity comparable to ara-CMP (ED$_{50}$=0.05 μM) and were more active than ara-C. However, prednisone-p-ara-C (II) and cortisol-p-ara-C (V) were found to be less active than both ara-CMP and ara-C.

TABLE 1

Effects of the Conjugates on the Viability of L-1210 Cells in Culture

| Compound | Concentration (μM) for 50 percent loss of viability at 72 hours |
|---|---|
| Pred-p-ara-C (I) | 0.05 |
| Prednisone-p-ara-C (II) | 0.5 |
| DXM-p-ara-C (III) | 0.08 |
| MePred-p-ara-C (IV) | 0.05 |
| Cortisol-p-ara-C (V) | 0.25 |
| Cortisone-p-ara-C (VI) | 0.07 |
| Ara-C | 0.1 |
| Ara-CMP | 0.05 |

EXAMPLE 12

Antitumor Activity Against Intraperitoneally (i.p.) Implanted L-1210 Leukemia in Mice The ascites cell form of L-1210 leukemia, grown in C$_3$D$_2$F$_1$/J female mice (supplied by Jackson Labs) were employed. The assay was performed according to National Cancer Institute (NCI) protocol 1.100 described by R. I. Gerau et al., Cancer Chemother. Rep. (Part 3) 3: (2): 7, 47 (1972) with a slight modification. Intraperitoneal implantation of $1 \times 10^6$ cells in 0.5-ml suspension to the control and the treated groups (each group comprised 8 C$_3$D$_2$F$_1$/J female mice, average wt 20 g) was carried out using donor mice (DBA/2Ha, supplied by Roswell Park Memorial Institute) bearing 3 day tumor growths. Compounds were dissolved in 0.9 percent NaCl and a 0.5 ml dose was administered intraperitoneally once daily. Treatment began 24 h after implantation and continued for 5 consecutive days. Control animals received a 0.5 ml injection of saline. Testing was followed as described in the NCI protocol and evaluated by recording the survival time according to the formula appearing in protocol 11. Table II shows the results.

TABLE II

Effects of the Conjugates on Survival of i.p. Implanted L-1210 Leukemic Mice[a]

| Compound | Dose[b] mg(μmol)/kg/day × 5 | Mean Survival Days[c] Treated | Control | Percent T/C[d] |
|---|---|---|---|---|
| Pred-p-ara-C (I) | 25 (37.5) | 14.63 | 9.50 | 154.0 |
|  | 40 (60.1) | 15.25 | 8.75 | 174.3 |
|  | 50 (75.0) | 19.13 | 9.50 | 201.4 |
|  | 75 (112.7) | 16.88 | 9.50 | 177.7 |
|  | 100 (150.0) | 11.74 | 8.63 | 136.2 |
| Prednisone-p-ara-C (II) | 25 (37.7) | 14.63 | 9.50 | 154.0 |
|  | 50 (75.4) | 18.13 | 8.63 | 210.0 |
|  | 75 (113.0) | 14.50 | 9.50 | 152.6 |
|  | 100 (150.7) | 10.88 | 8.75 | 124.0 |
|  | 200 (301.4) | 9.13 | 8.75 | 104.3 |
| DXM-p-ara-C (III) | 50 (71.7) | 13.50 | 9.00 | 150.0 |
| Cortisol-p-ara-C (V) | 50 (74.9) | 24.75 | 8.62 | 287.1 |
|  | 100 (149.8) | 14.25 | 9.25 | 154.1 |
| Cortisone-p-ara-C (VI) | 50 (75.1) | 20.14 | 9.00 | 223.8 |
| Ara-C | 25 (102.8) | 11.00 | 8.62 | 127.6 |

TABLE II-continued

Effects of the Conjugates on Survival of i.p. Implanted L-1210 Leukemic Mice[a]

| Compound | Dose[b] mg(μmol)/kg/day × 5 | Mean Survival Days[c] Treated | Control | Percent T/C[d] |
|---|---|---|---|---|
| | '50 (205.6) | 9.63 | 8.75 | 110.0 |
| Ara-CMP | 50 (154.7) | 9.13 | 8.75 | 104.3 |
| | 100 (309.4) | 11.00 | 9.00 | 122.2 |

[a]Each mouse received $1 \times 10^6$ cells intraperitoneally.
[b]Doses were administered intraperitoneally once daily to groups of 8 mice (ave. wt. 20g) for 5 consecutive days beginning 24 hours after tumor implantation.
[c]Mean survival days were calculated by the equation appearing in the NCI protocol.
[d]Mean survival days (treated/control) × 100.

The control mice died in 8–9 days with typical ascitic conditions. Since previous studies with ara-C against L-1210 bearing mice reported by J. S. Evans et al. in Cancer Res. 24: 1285 (1964) showed that the T/C ratio remained fairly constant between 20 and 70 mg/kg/day doses, 25 mg (102.8 μmol) and 50 mg (205.6 μmol)/kg/day dose was selected for ara-C for comparison. At this dose ara-C produced T/C of 128 percent and 110 percent, respectively, while ara-CMP at 50 mg (154.7 μmol) and 100 mg (309.4 μmol)/kg/day showed T/C of 104 percent and 122 percent, respectively. Prednisolone and prednisone showed T/C of 133 percent at 25 mg (69.4 μmol)/kg/day. The mice treated with conjugates I and II at doses between 25 and 75 mg/kg/day had no ascitic fluid and were very active at the end of the dosage period (5th day), but they started to accumulate ascitic fluid at the 15th day. Both conjugates I and II showed T/C of 154 percent at 25 mg (37.5 μmol)/kg/day. The most effective dose level of conjugates I, II, V and VI was 50 mg (75 μmol)/kg/day and gave T/C ratios of 201 percent, 210 percent and 224 percent, respectively, which is a remarkable therapeutic result based on ara-C content. However, DXM-p-ara-C (III) at 50 mg (71.7 μmol)/kg/day exhibited a somewhat less effective T/C of 150 percent and showed some toxicity.

At 75 mg (113 μmol)/kg/day dose, conjugates I and II showed T/C of 178 percent and 153 percent, respectively. These were less effective than at 5 mg/kg/day, and the compounds started to show toxicity at the higher dose (100 and 200 mg/kg/day). Conjugates I, II and V at 100 mg (150 μmol)/kg/day showed T/C ratios of 136 percent, 124 percent and 154 percent, respectively, while ara-CMP at a similar molar dose, 50 mg (155 μmol)/kg/day, gave a T/C of 104 percent which indicates that the conjugates may reduce the toxicity of ara-CMP. However, conjugate II at 200 mg (301 μmol)/kg/day showed a lower T/C (104 percent) than that (122 percent) of ara-CMP at a similar molar dose, 100 mg (309 μmol)/kg/day; this may reflect the additional toxicity of prednisone.

EXAMPLE 13

Comparison of Conjugates and Combinations

In order to determine if the conjugates are actually more effective than simply ara-C and the steroid given together, control assays wherein ara-C and various steroids were each given at the same molar concentration present in the conjugates were designed. Each mouse received $1 \times 10^6$ cells intraperitoneally. Doses were administered i.p. once daily to groups of 8 mice (avg. wt. 20 g) for 5 consecutive days beginning 24 hours after tumor implantation. In case of the combination, ara-C and the steroid were given at the same molar concentrations present in the conjugates. Mean survival days were calculated by the equation appearing in the NCI protocol; T/C ratios are reported in percent, i.e (treated/control) × 100. The results are shown in Table III.

At 75 μmol/kg/day dose, pred-p-ara-C (I) exhibited T/C of 201 percent, while the combination of ara-C and prednisolone each at the same molar dose gave T/C of only 144 percent. Similarly, at 114.7 μmol/kg/day dose, pred-p-ara-C (I) and a combination of ara-C and prednisolone showed T/C ratios of 178 percent and 106 percent, respectively. These results clearly demonstrate that the conjugates are superior to the combination of ara-C and glucocorticoids at various dose levels and that the toxicity of the conjugate, based on ara-C content, is substantially reduced.

TABLE III

Effects of The Ara-C Conjugates and Combination of Ara-C and Steroid on Survival of i.p. Implanted L1210 Leukemic Mice[a]

| Compd No. | Compound | Dose[b] μmole/kg/day × 5 | Weight change on Day 8 (g/mouse) | Survival Days Range | Mean (Treated/Control) | % T/C |
|---|---|---|---|---|---|---|
| I | Pred-p-ara-C | 75.0 | −0.28 | 15–36 | 19.13/9.5 | 201.4 |
| | Ara-C and Prednisolone | 75.0 each | −2.46 | 8–15 | 12.75/8.88 | 143.6 |
| II | Prednisone-p-ara-C | 75.4 | −0.30 | 15–21 | 18.13/8.63 | 210.0 |
| | Ara-C and Prednisone | 75.4 each | −1.25 | 12–15 | 13.25/9.13 | 145.1 |
| III | DXM-p-ara-C | 71.7 | −1.50 | 10–17 | 13.50/9.0 | 150.0 |
| | DXM-p-ara-C | 36.0 | −1.03 | 7–15 | 11.50/9.0 | 127.8 |
| | Ara-C and Dexamethasone | 36.0 each | −0.47 | 9–15 | 8.5/9.0 | 94.4 |
| IV | MePred-p-ara-C | 74.0 | −1.08 | 14–24 | 19.13/7.75 | 246.8 |
| | Ara-C and 6α-Methyl-prednisolone | 74.0 each | −1.38 | 9–17 | 13.13/9.13 | 143.8 |
| V | Cortisol-p-ara-C | 75.0 | '+0.09 | 21–32 | 24.75/8.62 | 287.1 |
| | Ara-C and Cortisol | 75.0 each | −1.05 | 12–15 | 13.50/9.13 | 147.9 |
| VI | Cortisone-p-ara-C | 75.1 | −0.07 | 15–35 | 21.43/9.0 | 238.1 |
| | Ara-C and Cortisone | 75.1 each | −1.79 | 13–18 | 14.17/9.13 | 161.6 |
| VII | Corticosterone-p-ara-C | 77.0 | −0.71 | 15–42 | 26.50/7.75 | 341.9 |
| | Ara-C and Corticosterone | 77.0 each | −1.48 | 8–23 | 12.75/9.13 | 139.6 |

TABLE III-continued

Effects of The Ara-C Conjugates and Combination of Ara-C and Steroid on Survival of i.p. Implanted L1210 Leukemic Mice[a]

| Compd No. | Compound | Dose[b] μmole/kg/day × 5 | Weight change on Day 8 (g/mouse) | Survival Days Range | Survival Days Mean (Treated/Control) | % T/C |
|---|---|---|---|---|---|---|
| VIII | DOC-p-ara-C | 78.7 | −0.94 | 17–24 | 21.38/9.0 | 237.5 |
|  | Ara-C and 11-Desoxy-corticosterone | 78.7 each | −4.25 | 9–12 | 10.38/9.33 | 111.3 |
| IX | Fludrocortisone-p-ara-C | 36.46 | −1.09 | 12–18 | 14.30/9.0 | 158.8 |
|  | Ara-C and Fludrocortisone | 36.46 each | −2.85 | 10–13 | 11.50/9.0 | 127.8 |

[a]Female $C_3D_2F_1/J$ mice in groups of 8 (ave wt 20 g) were inoculated i.p. with $1 \times 10^6$ lymphoid leukemia L1210 cells.
[b]Doses started 24 hours after tumor implantation.

EXAMPLE 14

Antitumor Activity Against Intracerebrally (i.c.) Implanted L-1210 in Mice

Effects of the conjugate on i.c. implanted L-1210 in mice were also studied. A mouse ($C_3D_2F_1/J$, female, avg. wt. 20 g) was anesthesized with diethyl ether, the right parietal scalp was washed with 70 percent ethanol, a 27 G ½ needle with a guard placed on the outside of the barrel 1.5 mm from the top of the bevel, was inserted through the skull and $1 \times 10^5$ cells in 0.05 ml suspension were inoculated into the mouse. The conjugate in 0.9 percent NaCl (0.5 ml) was administered intraperitoneally once daily. Treatment began 24 h after implantation and continued for 5 consecutive days. Control animals received a 0.5 ml injection of saline. Testing was followed as described in the NCI protocol and evaluated by recording the survival time according to the formula appearing in protocol 11.

Table IV shows the results. The control mice died in 9 days with heavy losses of body weight (5 g, 25 percent loss) and with severe exophthalmos. The mice treated with prednisone-p-ara-C (II), pred-p-ara-C (I) and cortisol-p-ara-C (V) also lost about 4 g of their body weight by day 11. However, the mice receiving conjugates I and V recovered from losing weight starting from day 15 and gained about 1 g over their original weight (20 g) by day 20. The mice treated with ara-C also lost about 5 g of their weight by day 14, and all but one of them died.

Conjugates I, II and V exhibited T/C of 201 percent, 183 percent and 228 percent respectively, while ara-C at the optimal dose (25 mg/kg/day) showed a T/C ratio of only 153 percent. These results again demonstrate that the conjugate is superior to ara-C.

TABLE IV

Effects of Ara-C Conjugates on Intracerebrally Implanted L-1210 in Mice[a]

| Compound | Dose[b] mg(μmol)/kg/day × 5 | Mean Survival Days[c] | Mean Survival Percent T/C[d] | Survivors on day 35 |
|---|---|---|---|---|
| Control | — | 9.00 | 100.0 | 0 |
| Ara-C | 25 (102.8) | 13.74 | 152.8 | 0 |
| Pred-p-ara-C (I) | 50 (75.0) | 18.13 | 201.4 | 1 |
| Prednisone-p-ara-C (II) | 50 (75.4) | 16.50 | 183.3 | 1 |
| Cortisol-p-ara-C (V) | 50 (74.9) | 20.50 | 227.8 | 2 |

[a]Each of 8 mice received $1 \times 10^5$ cells intracerebrally.
[b]Doses were administered intraperitoneally once daily to groups of 8 mice (ave. wt. 20 g) for 5 consecutive days beginning 24 hours after tumor implantation.
[c]Calculated by the equation appearing in the NCI protocol.
[d]Values as of 35th day.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

Since glucocorticoids readily penetrate the blood-brain-barrier (BBB) and enter both brain and cerebrospinal fluid (CSF), the conjugates can improve BBB penetrating properties of the nucleosides by providing a more lipophilic nature via conjugation with those steroids, e.g. glucocorticoids, which have specific receptors in the brain. the glucocorticoid moiety, once released from the conjugate by enzymatic hydrolysis, can be utilized for the treatment of cerebral edema caused by brain cancers in test animals. Once inside a cell, the conjugates are enzymatically hydrolyzed to release their nucleotide and steroid components.

What is claimed is:

1. A compound selected from the group consisting of compounds of the formula:

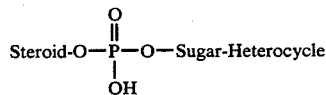

wherein:
steroid is a 21-hydroxy-1,4-pregnadiene-3,20-dione; 21-hydroxy-1,4-pregnadiene-3,11,20-trione; 21-hydroxy-4-pregnene-3,20-dione or 21-hydroxy-4-pregnene-3,11,20-trione which is unsubstituted or substituted by 1–3 hydroxy, methyl or fluoro groups at the 2α, 6α, 9α, 11, 16α, 17 or 18 positions and which is esterified to the phosphate moiety at the 21-position;
sugar is ribose, deoxyribose, lyxose, xylose or arabinose which is esterified to the phosphate moiety at the 5'-position and covalently bonded to the heterocycle moiety at the 1'-position to form a nucleoside; and heterocycle is a purine, pyrimidine, hydrogenated pyrimidine or triazolopurine nucleoside base; and the physiologically acceptable salts thereof.

2. A compound according to claim 1, wherein the steroid is selected from the group consisting of betamethasone, chloroprednisone, corticosterone, cortisone, desoxycorticosterone, dexamethasone, dichlorisone acetate, fluocinolone acetonide, fluorohydrocortisone, fluorometholone, fluprednisolone, flurandrenolone, hydrocortisone, methylprednisolone, paramethasone, prednisolone, prednisone and triamcinolone.

3. A compound according to claim 1, wherein the steroid is selected from the group consisting of:
11$\beta$,17$\alpha$,21-trihydroxy-1,4-pregnadiene-3,20-dione;
17$\alpha$,21-dihydroxy-1,4-pregnadiene-3,11,20-trione;
9$\alpha$-fluoro-11$\beta$,17$\alpha$,21-trihydroxy-16$\alpha$-methyl-1,4-pregnadiene-3,20-dione;
11$\beta$,17$\alpha$,21-trihydroxy-6$\alpha$-methyl-1,4-pregnadiene-3,20-dione; and
11$\beta$,17$\alpha$,21-trihydroxy-4-pregnene-3,20-dione.

4. A compound according to claim 1, wherein the steroid is selected from the group consisting of:
17$\alpha$,21-dihydroxy-4-pregnene-3,11,20-trione;
11$\beta$,21-dihydroxy-4-pregnene-3,20-dione;
4-pregnen-21-ol-3,20-dione;
21-hydroxy-4-pregnene-3,20-dione; and
9$\alpha$-fluoro-11$\beta$,17$\alpha$,21-trihydroxy-4-pregnene-3,20-dione.

5. A compound according to claim 1, wherein the steroid is selected from the group consisting of:
11$\beta$,21-Dihydroxy-3,20-dioxo-pregn-4-en-18-ol;
21-Hydroxy-pregna-4,6-diene-3,20 dione;
21-Hydroxy-2$\alpha$-methyl-pregn-4-ene 3,20-dione; and
11$\beta$,21-Dihydroxy-pregn-1,4-diene-3,20-dione.

6. A compound according to claim 1, wherein the steroid is selected from the group consisting of
16$\alpha$-Methyl-11$\beta$,17$\alpha$,21-trihydroxy-pregna-1,4-diene-3,20-dione;
11$\beta$,21-Dihydroxy-16$\alpha$-methyl-pregna-1,4-diene-3,20-dione;
9$\alpha$-Fluoro-11$\beta$,17$\alpha$,21-trihydroxy-16$\alpha$-methyl-pregn-4-ene-3,20-dione;
9$\alpha$-Fluoro-11$\beta$,17$\alpha$,21-trihydroxy-16$\beta$-methyl-pregna-1,4-diene-3,20-dione; and
9$\alpha$-Fluoro-11$\beta$,17$\alpha$,21-trihydroxy-16$\beta$-methyl-pregna-1,4-diene-3,20-dione.

7. A compound according to claim 1, wherein the steroid is selected from the group consisting of
9$\alpha$-Fluoro-11$\beta$,21-dihydroxy-16$\alpha$,17$\alpha$-[1-methylethylidene-bis(oxy)]-pregna-1,4-diene-3,20-dione;
9$\alpha$-Fluoro-11$\beta$,21-dihydroxy-16$\alpha$-methyl-pregna-1,4-diene-3,20-dione;
9$\alpha$-Fluoro-11$\beta$,21-dihydroxy-16$\alpha$-methyl-pregn-4-ene-3,20-dione;
6$\alpha$,9$\alpha$-Difluoro-11$\beta$,21-dihydroxy-16$\alpha$-methyl-pregn-4-ene-3,20-dione; and
9$\alpha$,11$\beta$-Dichloro-21-hydroxy-16$\alpha$-methyl-pregna-1,4-diene-3,20-dione.

8. A compound according to claim 1, wherein the sugar is ribose, deoxyribose or arabinose.

9. A compound according to claim 8, wherein the heterocycle is a purine or pyrimidine.

10. A compound according to claim 8, wherein the heterocycle is selected from the group consisting of cytosine, uracil, thymine, adenine, guanine, dihydrouracil, 5-fluorouracil, 5-azauracil, 6-azauracil, 5-azacytosine, 6-azacytosine, tetrahydropyridine dione, 2-amino tetrahydropyridine dione, 6-mercaptopurine, thioguanine, selenoguanine, 8-azaadenine-7-carboxyamide and N-methyl-2-amino-1,2,4-triazolopurine.

11. A compound according to claim 8, wherein the sugar and the heterocycle together form a nucleoside selected from the group consisting of 1-$\beta$-D-arabinofuranosylcytosine; 5-fluorodeoxyuridine; 5-azacytidine; 1-$\beta$-D-arabinofuranosyladenine; 6-mercaptopurine ribonucleoside; and tubercidin.

12. A compound according to claim 1, 5'-(prednisolone-21-phosphoryl)-1-$\beta$-D-arabinofuranosylcytosine.

13. A compound according to claim 1, 5'-(prednisone-21-phosphoryl)-1-$\beta$-D-arabinofuranosylcytosine.

14. A compound according to claim 1, 5'-(dexamethasone-21-phosphoryl)-1-$\beta$-D-arabinofuranosylcytosine.

15. A compound according to claim 1, 5'-(6$\alpha$-methylprednisolone-21-phosphoryl)-1-$\beta$-D-arabinofuranosylcytosine.

16. A compound according to claim 1, 5'-(cortisol-21-phosphory)-1-$\beta$-D-arabinofuranosylcytosine.

17. A compound according to claim 1, 5'-(cortisone-21-phosphoryl)-1-$\beta$-D-arabinofuranosylcytosine.

18. A pharmaceutical composition comprising a safe and cytotoxically effective amount of a compound according to any one of claims 12 thru 17 in combination with a pharmaceutically acceptable carrier.

19. A method for inhibiting the growth of cancer cells in a living body, which comprises administering a safe and cytotoxically effective amount of a compound according to any one of claims 12 thru 17 to a living test animal afflicted with cancer susceptible.

* * * * *